United States Patent [19]

Griffith et al.

[11] Patent Number: 4,855,462
[45] Date of Patent: Aug. 8, 1989

[54] ANTIHISTAMINES
[75] Inventors: Ronald C. Griffith, Pittsford; James J. Napier, Rochester, both of N.Y.
[73] Assignee: Pennwalt Corporation, Philadelphia, Pa.
[21] Appl. No.: 207,839
[22] Filed: Jun. 17, 1988
[51] Int. Cl.$^4$ .......................................... C07D 313/12
[52] U.S. Cl. .................................................... 549/354
[58] Field of Search ........................................ 549/354
[56] References Cited
U.S. PATENT DOCUMENTS
3,420,851 1/1969 Bloom et al. ...................... 260/333
4,395,420 7/1983 Bernstein .......................... 514/217
4,603,131 7/1986 Bernstein et al. .................. 514/220

FOREIGN PATENT DOCUMENTS
0966015 8/1964 United Kingdom ............... 549/354
1018995 2/1966 United Kingdom ............... 549/354

Primary Examiner—Glennon H. Hollrah
Assistant Examiner—Amelia A. Owens

[57] ABSTRACT

N-(Arylalkyl) dibenzoxepin propanamines useful as antihistamines, such as 3-dibenz[b,e]oxepin-11(6H)-ylidene-N-methyl-N-[6-[4-(1,1-dimethylethyl)phenyl]-6-oxohexyl]-1-propanamine hydrochloride.

4 Claims, No Drawings

ANTIHISTAMINES

BACKGROUND OF THE INVENTION

This invention relates to N-(arylalkyl) dibenzoxepin propanamine derivatives having useful antihistaminic activity with a low potential for sedation.

The utility of antihistamine compounds (histamine —$H_1$ antagonists) as a treatment for the alleviation of the symptoms of allergic disorders has been long recognized. However, due to their effects on the central nervous system, numerous side effects are observed with these agents, most notably sedation (Douglas, W. W. In: "The Pharmacological Basis of Therapeutics," 6th ed; Gilman, A. G.; Goodman, L. S.; Gilman, A.; Ed.; Macmillian: New York, 1980; pp. 622–632). For example, the tricyclic antidepressant doxepin (3-dibenz[b,e]oxepin-11(6H)-ylidene-N,N-dimethyl-1-propanamine) is a potent antagonist of histamine —$H_1$ receptors, but is known to cause sedation (Figge, J.; Leonard, P.; Richelson, E. *Eur. J. Pharm.*, 1979, 58 479–483). Because of its activity in the central nervous system, the use of doxepin in the treatment of allergic disorders has been limited to topical treatment (Bernstein, J. E.; Endicott, C. J. Eur. Pat. Appl. EP93373 A1; CA, 100, 39611h and Bernstein, J. E. U.S. Pat. No. 4,395,420; CA, 99, 128371h).

BRIEF SUMMARY OF THE INVENTION

This invention provides compounds of the formula (1):

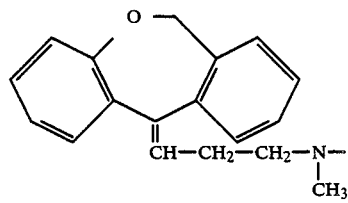

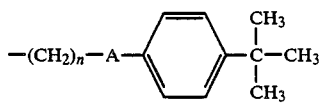

where n is a positive whole integer from 3 to 5 and A is —$CH_2$—, —CH(OH)— or —C(=O)—, geometric and enantiomeric forms thereof, and pharmaceutically acceptable acid addition salts thereof. Preferred compounds are those in which n is 5 and A is —C(=O)— and those in which n is 4 and A is —$CH_2$—.

DETAILED DESCRIPTION OF THE INVENTION

It has now been found that the N-(arylalkyl) dibenzoxepin propanamine compounds summarized above posess antihistaminic activity with a low potential for sedation.

The compounds of formula (1) are capable of existing as cis and trans olefinic isomers; additionally, stereoisomeric forms of each geometric isomer will exist when an asymmetric center is present in the compound. This invention relates to all cis and trans isomeric forms and stereoisomeric forms as well as mixtures thereof.

The compounds of this invention may be prepared by several methods. Three procedures which represent the preferred methods for the preparation of the compounds of this invention are designated Method A, Method B, and Method C.

Method A comprises reacting the readily available 3-dibenz[b,e]oxepin-11(6H)-ylidene-N-methyl-1-propanamine (2) with a compound of formula (3):

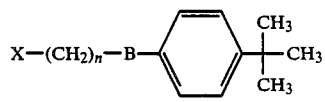

wherein X is chlorine or bromine; n is a positive whole integer from 3 to 5; and B is —$CH_2$— or C(=O)—; in an inert solvent, such as toluene or dimethylformamide, in the presence of a base, such as potassium bicarbonate, with or without a catalytic amount of potassium iodide to provide the corresponding compounds of formula (1) where n is a positive whole integer of 3 to 5; and A is —$CH_2$— or —C(=O)—.

In Method B an amide bond is formed between amine (2) and a carboxylic acid of formula (4):

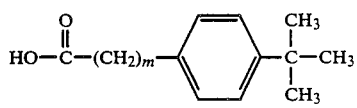

wherein m is a whole integer of 3 to 5, to provide an amide of formula (5):

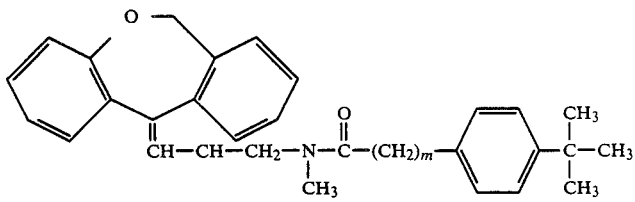

wherein m is as defined above. This amide bond formation may be carried out using standard acylation methods. The preferred method is the reaction of a carboxylic acid of formula (4) with dicyclohexylcarbodiimide and 1-hydroxysuccinimide in an inert solvent, such as tetrahydrofuran, to produce the corresponding N-hydroxysuccinimide ester, which can be reacted with amine (2) in an inert solvent, such as tetrahydrofuran or dimethylformamide or mixtures thereof to produce an amide of formula (5). Amides of formula (5) can be reacted with suitable reducing agents, such as lithium aluminum hydride, in an appropriate solvent, such as tetrahydrofuran or diethyl ether or mixtures thereof to produce the corresponding compounds of formula (1) where n is as defined above and A is —$CH_2$—.

Method C comprises reacting a compound of formula (1) where n is as defined above and A is —C(=O)— with a suitable reducing agent, such as sodium borohydride, in an appropriate solvent such as a lower alkanol, for example methanol or ethanol, to provide the corresponding compounds of formula (1) where n is as defined above and A is —CH(OH)—.

Compounds of the formula (2) (3) and (4) are known or can be made by known methods.

The compounds of formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, fumaric, malic, maleic, tartaric, citric, benzoic, methanesulfonic, 4-methylbenzenesulfonic or carbonic acid.

Antihistaminic activity is measured by the compounds ability to inhibit the wheal response to histamine in a rat dermal vascular permeability test. Groups of 10 male rats are administered the test compound orally one hour prior to an intravenous injection of 1 mL of a 0.5% Evans Blue dye into naive animals. Ten minutes later the animals are challenged by intradermal injection of 0.1 mL of solutions of histamine at 10 µg, 2 µg and 0.5 µg per 0.1 mL to separate sites on the back. Five minutes following the histamine injections the animals are killed, the skin reflected and the mean diameter of the three wheals determined. The percent inhibition is calculated as the difference in mean diameter between the control and the drug treated group divided by the control diameter times 100. Compounds of the formula (1) caused a 50% inhibition of the wheal respone to the 0.5 µg histamine treatment at doses of 10 mg/kg and less. In particular the compound of Example 2 caused a 70% inhibition of the wheal response at a dose of 10 mg/kg.

The sedative effects of the compounds are observed by behavioral observation of groups of mice or rats. Sedative effects were generally not observed for oral doses of the compounds of formula (1) of 200 mg/kg or less.

The following non-limiting illustrations and examples are provided to exemplify the preparation of compounds of formula (1).

The compounds of Examples B 1 through 9 were prepared from the stereoisomeric mixture of 3-dibenz[b,e]oxepin-11(6H)-ylidene-N-methyl-1-propanamine hydrochloride as described in Illustration 1 and were obtained as a mixture of olefinic stereoisomers.

ILLUSTRATION 1

Preparation of 3-Dibenz[b,e]oxepin-11(6H)-ylidene-N-methyl-1-propanamine hydrochloride This compound was prepared by suitable modification of the procedure described by Bickelhaupt, F., Stach, K., Thiel, M., *Monatsh.*, 1964, 95, 485 as follows. To a stirred solution of ethyl chloroformate (188 mL, 1.97 mol) in toluene (200 mL) at 85° C. under nitrogen was added a solution of 3-dibenz[b,e]oxepin-11(6H)-ylidene-N,N-dimethyl-1-propanamine (184.6 g, 0.658 mol) in toluene (350 mL) and the mixture was stirred at that temperature for 6 hours. The solvents were evaporated and the residual oil was dissolved in toluene (1 L) and washed with 10% HCl (3×100 mL). The toluene solution was dried over magnesium sulfate and the solvent evaporated to give 166.8 g of an oil. To a stirred solution of this oil in 95% ethanol (525 mL) was added potassium hydroxide (137.7 g, 246 mol) and the solution was heated to reflux under nitrogen for 24 hours. The reaction was cooled to ambient temperature, poured into water (3 L), acidified with conc. HCl and washed with toluene (4×500 mL). The aqueous layer was basified with 50% sodium hydroxide and extracted with chloroform (3×1 L). The combined chloroform extracts were dried over magnesium sulfate and the solvent evaporated to give 103 g of an oil. The above oil was dissolved in methanol (200 mL) and ethyl acetate (300 mL) and acidified with HCl gas. The solid which formed was isolated by filtration to give 99.1 g of 3-dibenz[b,e]oxepin-11(6H)-ylidene-N-methyl-1-propanamine (5:1 mixture of E:Z isomers), mp 236°–237° C.

A 20.0 g sample of the above product was recrystallized twice from 2-propanol, and vacuum dried at 75° C. for 72 hours to provide 12.2 g of E-3-dibenz[b,e]oxepin-11(6H)-ylidene-N-methyl-1-propanamine, mp 240°–242° C.

ILLUSTRATION 2

Preparation of 1-[4-(1,1-Dimethylethyl)phenyl]-4-chlorobutanone

This compound was prepared by suitable modification of the procedure described by Westeringh, C. van der; Hermans, B.; Raeymaekers, F.; Eycken, C. van der, *Ind. Chim-Belge.*, 1960, 25, 1073 as follows. To a stirred solution of 4-chlorobutyryl chloride (72.4 mL, 0.647 mol) in dichloromethane (1 L) at 5° C. under nitrogen was added aluminum chloride (94.6 g, 0.71 mol) and the mixture was stirred for 1 hour. To this mixture was added dropwise a solution of t-butylbenzene (100 mL, 0.647 mol) in dichloromethane (100 mL). The reaction was warmed to ambient temperature and stirred at that temperature overnight. The reaction was poured onto a mixture of ice (1 L) and 0.5N HCl (1 L). The phases were separated and the aqueous phase was extracted with dichloromethane (2×300 mL). The combined dichloromethane extracts were washed with 5% NaOH (2×300 mL) and saturated NaCl (250 mL), dried over magnesium sulfate and the solvent removed to give 149.8 g of an oil. This oil was crystallized from hexanes (150 mL) to provide 118.3 g of 1-[4-(1,1-dimethylethyl)phenyl]-4-chlorobutanone, mp 46°–49° C.

ILLUSTRATION 3

Preparation of 4-[4-(1,1-Dimethylethyl)phenyl]butanoic acid

This compound was prepared by suitable modification of the procedures described by Martin, E. L., *J. Am. Chem. Soc.*, 1936, 58, 1841 as follows. To a stirred suspension of aluminum chloride (266 g 2.0 mol) in dichloromethane (1 L) cooled in an ice water bath under a nitrogen atmosphere was added succinic anhydride (100 g, 1.0 mol). The mixture was warmed to ambient temperature and a solution of t-butylbenzene (122.4 g, 0.897 mol) in dichloromethane was added dropwise. The reaction was stirred at ambient temperature for 16 hours. The reaction was poured onto 2N HCl and extracted with chloroform (2×800 mL). The combined organic extracts were washed with saturated NaCl, dried over magnesium sulfate and the solvent evaporated to give 156.6 g of a tan solid. Recrystallization from toluene (700 mL) and hexanes (200 mL) gave 94.5 g of 4-[4-(1,1-dimethylethyl)-phenyl]-4-oxobutanoic acid, mp 112°–114° C.

To a stirred suspension of zinc amalgam (180 g) in water (150 mL) were carefully added conc. HCl (325 mL), toluene (150 mL), acetic acid (40 mL), and 4-[4-(1,1-dimethylethyl)phenyl]-4-oxobutanoic acid (45 g, 0.19 mol). The reaction was heated to reflux for 24 hours. The reaction was cooled to ambient temperature, the solution decanted and extracted with ether (3×300 mL). The combined ether extracts were washed with saturated sodium chloride (300 mL), dried over magnesium sulfate, and concentrated to give 42.2 g of an off-white solid. Recrystallization from hexanes gave 25.0 g of 4-[4-(1,1-dimethylethyl)phenyl]butanoic acid, mp 55°–57° C.

ILLUSTRATION 4

Preparation of 4-[4-(1,1-Dimethylethyl)phenyl]-1-bromobutane

To a stirred suspension of lithium aluminum hydride (4.0 g, 0.105 mol) in THF (100 mL) at 0° C. under a nitrogen atmosphere was added a solution of 4-[4-(1,1-dimethylethyl)-phenyl]butanoic acid (10.31 g, 0.0455 mol) in THF (80 mL). The reaction was heated to reflux for 6 hours. The reaction was cooled to 0° C. and water (4 mL), 15% NaOH (4 mL) and water (12 mL) were carefully added. Ethyl ether (150 mL) was added, the mixture warmed to ambient temperature, and the precipitated salts were removed by filtration. Removal of solvent gave 9.15 g of 4-[4-(1,1-dimethylethyl)phenyl]-butanol as a colorless oil.

To a stirred solution of phosphorous tribromide (1.75 mL, 0.185 mol) in benzene (100 mL) at 8° C. was added a solution of 4-[4-(1,1-dimethylethyl)phenyl]butanol (9.15 g, 0.0444 mol) in benzene (50 mL). The solution was stirred at 10° C. for 2 hours, water (200 mL) was added, and the mixture was extracted with ethyl ether (2×150 mL). The combined ether extracts were washed with water (2×150 mL) and saturated NaCl (150 mL) and dried over magnesium sulfate. Removal of solvent gave 11.6 g of an oil. This oil was purified by silica gel chromatography, eluting with 5% ethyl acetate-hexane, to give 3.16 g of 4-[4-(1,1-dimethylethyl)-phenyl]-1-bromobutane as a colorless oil; NMR $\delta$, 1.37 (S, 9H), 1.8 (m, 2H), 2.45 (t, J=7 Hz, 2H), 3.38 (t, J=7 HZ, 2H), 7.1, 7.3 (ABq, J=9.5 HZ, 4H).

EXAMPLE 1

Preparation of 3-Dibenz[b,e]oxepin-11(6H)-ylidene-N-methyl-N-[6-[4-(1,1-dimethylethyl)phenyl]-6-oxohexyl]-1-propanamine hydrochloride

Method A

To a stirred solution of 3-dibenz[b,e]oxepin-11(6H)-ylidene-N-methyl-1-propanamine (10.0 g, 0.033 mol) in DMF (80 mL) were added 6-bromo-1-[4-(1,1-dimethylethyl)phenyl]-1-hexanone (10.3 g, 0.033 mol) and potassium bicarbonate (6.6 g, 0.066 mol). The mixture was heated to 75°–80° C. under nitrogen for 28 hours. The reaction was cooled to ambient temperature, diluted with water (300 mL) and extracted with ethyl acetate (2×150 mL). The combined ethyl acetate extracts were washed with water (3×150 mL) and saturated NaCl (100 mL) and dried over magnesium sulfate. Removal of solvent gave an oil of 17.1 g. This oil was dissolved in 2-propanol (100 mL) and acidified with HCl gas. The solution was diluted to 400 mL with anhydrous ether and cooled. The solid was collected by filtration, recrystallized twice from ethyl acetate-methanol (15:1), and vacuum dried at 70° C. for 92 hours to provide 5.69 g of 3-dibenz[b,e]oxepin-11(6H)-ylidene-N-methyl-N-[6-[4-(1,1-dimethylethyl)phenyl]-6-oxohexyl]-1-propanamine hydrochloride, mp 159°–161° C.

EXAMPLE 2

Preparation of 3-Dibenz[b,e]oxepin-11(6H)-ylidene-N-methyl-N-[4-(1,1-dimethylethyl)phenyl]-4-oxobutyl]-1-propanamine hydrochloride To a solution of 3-dibenz[b,e]oxepin-11(6H)-ylidene-N-methyl-1-propanamine (12.2 g, 0.046 mol) in toluene (100 mL) were added potassium bicarbonate (8.0 g, 0.08 mol), 1-[4-(1,1-dimethylethyl)phenyl-4-chloro-1-butanone (12.1 g, 0.051 mol), and potassium iodide (0.6 g, 0.0036 mol).

The mixture was heated to 95°–100° C. for 80 hours under a nitrogen atmosphere. The solution was cooled to ambient temperature, diluted with water (200 mL) and extracted with ethyl acetate (2×200 mL). The combined ethyl acetate extracs were washed with saturated NaCl and dried over MgSO4. Removal of solvent gave an oil of 21.7 g. This oil was dissolved in 2-propanol (100 mL) and acidified with HCl gas. Ether (150 mL) was added and the solid which formed was collected by filtration to give an off-white solid of 13.9 g.

The above solid was treated with 5% sodium hydroxide (100 mL) and extracted with chloroform (2×100 mL). The combined chloroform extracts were dried and evaporated to give an oil of 12.8 g. The above oil was purified by chromatography on a Waters Prep 500 HPLC on silica gel, eluting with 3% ammoniated methanol-chloroform. The fractions containing the desired products were combined and the solvents removed to give 10.7 g of an oil.

The above oil was dissolved in 2-propanol (100 mL) and acidified with HCl gas. Ether (250 mL) was added and the solid was collected by filtration to give 11.3 g of a white solid, mp 198°–203° C. A 6.5 g sample of the above solid was recrystallized from 2-propanol:methanol (3:2) and vacuum dried at 80° C. for 48 hours to provide 5.0 g of 3-dibenz[b,e]-oxepin-11(6H)-ylidene-N-methyl-N-[4-[4-(1,1-dimethylethyl)-phenyl]-4-oxobutyl]-1-propanamine hydrochloride; mp 209°–212° C.

EXAMPLE 3

Preparation of 3-Dibenz[b,e]oxepin-11(6H)-ylidene-N-methyl-N-[4-hydroxy-4-[4-(1,1-dimethylethyl)phenyl]butyl]-1-propanamine 4-methylbenzenesulfonic acid (1:1) salt

Method C

To a stirred solution of 3-dibenz[b,e]oxepin-11(6H)-ylidene-N-methyl-N-[4-[4-(1,1-dimethylethyl)phenyl]-4-oxo-butyl]-1-propanamine hydrochloride (6.1 g, 0.013 mol) in methanol (100 mL) was added enough 15% sodium hydroxide to give a basic solution. The solution was cooled in an ice-water bath, under a nitrogen atmosphere, and sodium borohydride (0.96 g, 0.025 mol) was added in portions. The reaction slowly warmed to ambient temperature and was stirred at that temperature for 3 hours. Acetone (10 mL) was added and the solvents were removed under vacuum. The residue was dissolved in water (100 mL) and extracted with dichloromethane (3×100 mL). The combined dichloromethane extracts were washed with saturated NaCl (100 mL), dried and the solvent evaporated to give 6.3 g of an oil. The above oil was purified by chromatography on a Waters Prep 500 HPLC on silica gel eluting with 3% ammoniated methanol-chloroform. The fractions containing the desired product were combined and the solvents evaporated to give 5.6 g of an oil. This oil was dissolved in ethyl acetate (100 mL), decolorized with carbon, and the solvent removed to give 4.9 L g of a colorless oil.

The above oil was dissolved in methanol (100 mL) and 4-methylbenzenesulfonic acid monohydrate (2.0 g, 0.01 mol) was added. The solution was stirred at ambient temperature for a few minutes and the solvent was removed. The residue was dissolved in ethyl acetate (30 mL) and ether (15 mL). The solid which formed was collected by filtration and vacuum dried at 30° C. for 72 hours to provide 3.9 g of 3-dibenz[b,e]oxepin-11(6H)-ylidene-N-methyl-N-[4-hydroxy-4-[4-(1,1-dimethylethyl)phenyl]butyl]-1-propanamine 4-methylbenzenesulfonic acid (1:1) salt, mp 140°-144° C.

EXAMPLE 4

Preparation of
3-Dibenz[b,e]oxepin-11(6H)-ylidene-N-methyl-N-[6-[4-(1,1-dimethylehyl)phenyl]hexyl]-1-propanamine hydrochloride Method B To a stirred solution of 6-[4-(1,1-dimethylethyl)-phenyl]hexanoic acid (10.5 g, 0.0432 mol) in tetrahydrofuran (150 mL) were added N-hydroxysuccinimide (4.86 g, 0.0423 mol) and dicyclohexylcarbodiimide (8.72 g, 0.0423 mol). The reaction was stirred at ambient temperature under nitrogen for 1.5 hours. The precipitated solid was removed by filtration. To a stirred solution of the filtrate, at ambient temperature under nitrogen, was added a solution of 3-dibenz[b,e]oxepin-11(6H)-ylidene-N-methyl-1-propanamine (11.2 g, 0.0423 mol) in tetrahydrofuran (120 mL) and the reaction was stirred at ambient temperature for 22 hours. The mixture was filtered, the solvent evaporated, and the residue dissolved in ethyl acetate (250 mL). The ethyl acetate solution was washed with water (1×200 mL), 1N HCl (200 mL), 2N sodium carbonate (200 mL), and saturated NaCl (200 mL) and dried over magnesium sulfate. Removal of solvent gave 26.2 g of an oil. The above oil was purified by silica gel chromatography on a Waters Prep 500 HPLC, eluting with chloroform. The fractions containing the desired product were combined and the solvents evaporated to give 15.4 g of 3-dibenz[b,e]oxepin-11(6H)-ylidene-N-methyl-N-[6-[4-(1,1-dimethylethyl)phenyl]-1-oxohexyl]-1-propanamine as an oil.

To a stirred solution of the above oil (15.2 g, 0.0307 mol) in anhydrous ether (700 mL) at 0° C. under nitrogen was added lithium aluminum hydride (6.90 g, 0.182 mol) and the mixture was stirred for 45 min. Water (7 mL), 15% NaOH (7 mL) and water (21 mL) were carefully added. The reaction mixture was warmed to ambient temperature and the precipitated solids were removed by filtration. The filtrates was concentrated under vacuum to give 12.38 g of an oil. This oil was dissolved in 2-propanol (30 mL) and ether (170 mL) and acidified with HCl gas. The solid was collected by filtration, recrystallized from ethyl acetate (150 mL) and methanol (20 mL), and vacuum dried at 70° C. for 48 hours to provide 6.93 g of 3-dibenz[b,e]oxepin-11(6H)-ylidene-N-methyl-N-[6-[4-(1,1-dimethylethyl)-phenyl]hexyl]-1-propanamine hydrochloride, mp 161°-163° C.

EXAMPLE 5

Preparation of
3-Dibenz[b,e]oxepin-11(6H)-ylidene-N-methyl-N-[4-[4-(1,1-dimethylethyl)phenyl]butyl]-1-propanamine hydrochloride By procedures essentially the same as those described in Example 1, and by substituting 1-bromo-4-[4-(1,1-dimethylethyl)phenyl]butane for 6-bromo-1-[4-(1,1-dimethylethyl)-phenyl]-1-hexanone; the corresponding 3-dibenz[b,e]oxepin-11(6)-ylidene-N-methyl-N-[4-[4-(1,1-dimethylethyl)phenyl]-butyl]-1-propanamine hydrochloride, mp 184°-186° C., was prepared.

Or, by procedures essentially the same as those described in Example 4, and by substituting 4-[4-(1,1-dimethylethyl)phenyl]butanoic acid for 6-[4-(1,1-dimethylethyl)phenyl]hexanoic acid; the corresponding 3-dibenz[b,e]oxepin-11(6H)-ylidene-N-methyl-N-[4-[4-(1,1-dimethylethyl)phenyl]butyl]-1-propanamine hydrochloride, mp 184°-186° C., was prepared.

EXAMPLE 6

Preparation of
3-Dibenz[b,e]oxepin-11(6H)-ylidene-N-methyl-N-[5-[4-(1,1-dimethylethyl)phenyl]-5-oxopentyl]-1-propanamine hydrochloride By procedures essentially the same as those described in Example 1, and by substituting 5-chloro-1-[4-(1,1-dimethylethyl)phenyl]-1-pentanone for 6-bromo-1-[4-(1,1-dimethylethyl)phenyl]-1-hexanone; the corresponding 3-dibenz[b,e]oxepin-11(6H)-ylidene-N-methyl-N-[5-[4-(1,1-dimethylethyl)phenyl]-5-oxopentyl]-1-propanamine hydrochloride, mp 142°-145° C., was prepared.

EXAMPLE 7

Preparation of
3-Dibenz[b,e]oxepin-11(6H)-ylidene-N-methyl-N-[5-[4-(1,1-dimethylethyl)phenyl]pentyl]-1-propanamine hydrochloride By procedures essentially the same as those described in Example 4, and by substituting 5-[4-(1,1-dimethylethyl)-phenyl]pentanoic acid for 6-[4-(1,1-dimethylethyl)phenyl]-hexanoic acid; the corresponding 3-dibenz[b,e]oxepin-11(6H)-ylidene-N-methyl-N-[5-[4-(1,1-dimethylethyl)phenyl]pentyl]-1-propanamine hydrochloride, mp 150°-151° C., was prepared.

EXAMPLE 8

Preparation of
3-Dibenz[b,e]oxepin-11(6H)-ylidene-N-methyl-N-[5-hydroxy-5-[4-(1,1-dimethylethyl)phenyl]pentyl]-1-propanamine By procedures essentially the same as those described in Example 3, and by substituting 3-dibenz[b,e]oxepin-11(6H)-ylidene-N-methyl-N-[5-[4-(1,1-dimethylethyl)-phenyl]-5-oxo-pentyl]-1-propanamine hydrochloride for 3-dibenz[b,e]oxepin-11(6H)-ylidene-N-methyl-N-[4-[4-(1,1-dimethylethyl)phenyl]-4-oxobutyl]-1-propanamine hydrochloride; the corresponding 3-dibenz[b,e]oxepin-11(6H)-ylidene-N-methyl-N-[5-hydroxy-5-[4-(1,1-dimethylethyl)phenyl]pentyl]-1-propanamine was prepared as an oil; NMR δ, 1.2-2.6 (m, 13H), 1.33 (s, 9H), 2.13, 2.25 (two s (5:1 ratio), 3H), 4.5-5.8 (broad S, 2H), 4.63 (t, J=7 Hz, 1H), 6.06, 5.72 (two t (5:1 ratio), J=7 Hz, 1H), 6.77 (d, J=8 Hz, 1H), 6.88 (t, J=8 Hz, 1H), 7.0-7.5 (m, 10H).

EXAMPLE 9

Preparation of 3-Dibenz[b,e]oxepin-11(6H)-ylidene-N-methyl-N-[6-hydroxy-6-[4-(1,1-dimethylethyl)phenyl]hexyl]-1-propanamine By procedures essentially the same as those described in Example 3, and by substituting 3-dibenz[b,e]oxepin-11(6H)-ylidene-N-methyl-N-[6-[4-(1,1-dimethylethyl)-phenyl]-6-oxo-hexyl]-1-propanamine hydrochloride for 3-dibenz[b,e]oxepin-11(6H)-ylidene-N-methyl-N-[4-[4-(1,1-dimethylethyl)phenyl]-4-oxobutyl]-1-propanamine hydrochloride; the corresponding 3-dibenz[b,e]oxepin-11(6H)-ylidene-N-methyl-N-[6-hydroxy-6-[4-(1,1-dimethylethyl)phenyl]hexyl]-1-propanamine, mp 73°-75° C., was prepared.

EXAMPLE 10

Preparation of E-3-Dibenz[b,e]oxepin-11(6H)-ylidene-N-methyl-N-[4-[4-(1,1-dimethylethyl)phenyl]-4-oxobutyl]-1-propanamine hydrochloride By procedures essentially the same as those described in Example 2, and by substituting E-3-dibenz[b,e]oxepin-11(6H)-ylidene-N-methyl-1-propanamine for 3-dibenz[b,e]oxepin-11(6H)-ylidene-N-methyl-1-propanamine (5:1 mixture of E:Z isomers); the corresponding E-3-dibenz[b,e]oxepin-11(6H)-ylidene-N-methyl-N-[4-[4-(1,1-dimethylethyl)phenyl]-4-oxobutyl]-1-propanamine hydrochloride, mp 217°-218° C., was prepared.

What is claimed is:

1. A compound of the formula:

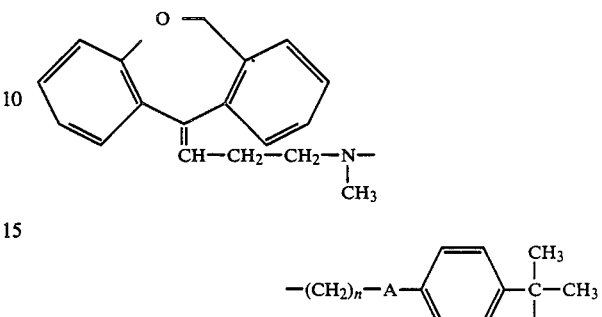

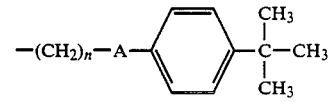

wherein n is a positive whole integer from 3 to 5 and A is —CH$_2$—, —CH(OH)— or —C(=O)—, all geometric and enantiomeric forms thereof, and pharmaceutically acceptable acid addition salts thereof.

2. A compound as in claim 1 wherein n is 5 and A is —C(=O)—.

3. A compound as in claim 1 wherein n is 4 and A is —CH$_2$—.

4. A compound of claim 1, 3-dibenz[b,e]oxepin-11(6H)-ylidene-N-methyl-N-[4-hydroxy-4-[4-(1,1-dimethylethyl)-phenyl]butyl]-1-propanamine 4-methylbenzenesulfonic acid (1:1) salt.

* * * * *